United States Patent
Kelly

(10) Patent No.: US 9,873,717 B2
(45) Date of Patent: Jan. 23, 2018

(54) TRH BINDING SITE IN HUMAN CNS

(71) Applicant: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN, Dublin (IE)

(72) Inventor: Julie Kelly, Dublin (IE)

(73) Assignee: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN, Dublin (IE)

( * ) Notice: Subject to any disclaimer, the term of this patent is extended or adjusted under 35 U.S.C. 154(b) by 0 days.

(21) Appl. No.: 14/653,688

(22) PCT Filed: Dec. 18, 2013

(86) PCT No.: PCT/EP2013/077221
§ 371 (c)(1),
(2) Date: Jun. 18, 2015

(87) PCT Pub. No.: WO2014/096090
PCT Pub. Date: Jun. 26, 2014

(65) Prior Publication Data
US 2015/0361136 A1  Dec. 17, 2015

(30) Foreign Application Priority Data
Dec. 19, 2012  (IE) .................................... 2012/0542

(51) Int. Cl.
G01N 33/483  (2006.01)
C07K 7/06  (2006.01)
C07K 14/72  (2006.01)
C07K 5/117  (2006.01)
G01N 33/74  (2006.01)
A61K 38/00  (2006.01)

(52) U.S. Cl.
CPC .............. *C07K 7/06* (2013.01); *C07K 5/1024* (2013.01); *C07K 14/723* (2013.01); *G01N 33/74* (2013.01); *A61K 38/00* (2013.01); *G01N 2333/726* (2013.01); *G01N 2500/04* (2013.01); *G01N 2500/10* (2013.01)

(58) Field of Classification Search
None
See application file for complete search history.

(56) References Cited

U.S. PATENT DOCUMENTS 7,713,935 B2 *  5/2010  Kelly ....................... C07K 7/06
                                                            514/17.7

FOREIGN PATENT DOCUMENTS

WO  WO2006/038206  *  4/2006

OTHER PUBLICATIONS

Hogan et al., Neuroscience Letters, 431(1):26-30, 2007.*
Scalabrino et al., Neuropharmacology, 52:1472-1481, 2007.*

* cited by examiner

Primary Examiner — Kimberly A. Ballard
Assistant Examiner — Stacey MacFarlane
(74) Attorney, Agent, or Firm — Foley & Lardner LLP; Antoinette F. Konski; Peng Sun

(57) ABSTRACT

The invention relates to a novel thyrotropin releasing hormone (TRH) receptor subtype in human central nervous system (CNS) that is pharmacologically distinct from the TRH receptor subtype in human pituitary. The invention provides a means to understand how the central actions of TRH are mediated and to isolate and characterize the novel receptor, as well as methods applicable to research and development of diagnostic and therapeutic applications in human CNS disorders.

7 Claims, No Drawings

TRH BINDING SITE IN HUMAN CNS

CROSS-REFERENCE TO RELATED APPLICATIONS

This application is a national phase application under 35 U.S.C. §371 of International Application No. PCT/EP2013/077221, filed Dec. 18, 2013, which in turn claims priority to Irish Application No. 2012/0542, filed Dec. 19, 2012, the entire content of each of which is incorporated herein by reference.

FIELD OF THE INVENTION

The present invention relates to the identification of a novel TRH receptor (TRHR) subtype in human central nervous system (CNS) tissue that is pharmacologically distinct from the known TRH receptor subtype found in human pituitary tissue. The distinction is based on discriminatory ligand binding characteristics of TRH-based compounds such as Glp-Asn-Pro-DTyr-DTrp-NH$_2$ and its structurally related analogs at these receptor sites. The invention thus provides a means for the identification of ligands that will discriminate between TRHR subtypes in the CNS and pituitary. In addition, the invention provides a tool with which to distinguish between CNS TRHR-mediated and pituitary-mediated biological effect. The invention also provides methods to facilitate the design of drugs which can bind the TRH receptors in the CNS in order to treat CNS disorders that currently have unmet need. These include, but are not limited to, neurological disorders involving neuronal injury or disturbances in neuronal functioning, such as depression, intractable epilepsy, and acute and chronic neurodegeneration, which include for example, brain and spinal cord injury, stroke, pain, Amyotrophic Lateral Sclerosis (ALS, also known as Motor Neuron Disease (MND) and Lou Gehrig's disease), spinocerebellar ataxia (SCA), Alzheimer's disease (AD), and Parkinson's disease (PD).

BACKGROUND TO THE INVENTION

Thyrotropin releasing hormone (TRH) occurs naturally in humans and is recognized to have multifaceted, homeostatic, neuroprotective and neurotrophic effects in the central nervous system (CNS), which are Independent of its endocrine actions. These CNS effects of TRH provide the basis for its clinical use in the treatment of CNS-related disorders and may confer significant advantages for TRH-based compounds over other prospective neurotherapeutics directed towards a single injury mechanism, particularly in complex CNS disease states, such as neurodegenerative disorders. Potential clinical applications of TRH and TRH-related compounds in human CNS-related disorders include, but are not limited to, depression, chronic fatigue syndromes, narcolepsy, neurasthenia, lethargy, sedation secondary to drugs, chemo- or radiation therapy, sedative intoxication/respiratory distress, recovery from general anaesthesia, attention deficit/hyperactive disorder (ADHD), disturbances of circadian rhythm (e.g. jet lag), bipolar affective disorder, anxiety disorders, Alzheimer's disease and other dementias with cognition deficits, frontotemporal lobe dementia, seizure disorders, obesity and motor neuron disorders and pain. Clinical use of TRH is limited, however, by its short half life and potential endocrine side effects. U.S. Pat. No. 7,713,935 B2 describes how Glp-Asn-Pro-DTyr-DTrp-NH2 overcomes these drawbacks and offers a means to harness therapeutic benefits of central TRH actions in the treatment of a wide range of CNS disorders.

The biological actions of neuroactive peptides, such as naturally-occurring TRH, are mediated by specific receptors. Ligand-receptor interaction can be measured by radioligand binding studies or less directly through assessment of dose-response curves for a biological effect. The former requires a radiolabelled form of the ligand and a source of receptors, such as a cell membrane fraction, intact cells or solubilised preparations. The receptors and ligand are incubated together until equilibrium is reached and the amount of labelled ligand bound to the receptors is determined. When homogenised tissue/particulate preparations are used, this may be accomplished by filtration, centrifugation or equilibrium dialysis which separate free ligand from receptor-bound ligand. With soluble tissue preparations this separation of bound from free may be achieved by gel filtration, equilibrium dialysis, and/or precipitation of the receptor-bound ligand. Ligand binding screening assays are useful to identify new compounds that target a receptor. Competition binding assays, in which an unlabelled test compound is tested for its ability to displace the radiolabelled ligand, can be used to determine the affinity of such other compounds for the receptor site. Autoradiography employing radiolabelled ligand can be used to localize and map regional receptor distribution, estimate the CNS uptake of ligand, and carry out pharmacokinetic evaluations.

[$^3$H][3-Me-His$^2$]TRH is typically employed to label high affinity TRH receptor sites in radioligand binding studies since it binds with greater affinity and affords higher specific binding than [$^3$H]TRH.

A limited number of radioligand binding studies employing human brain tissue have been described. These studies have shown that [$^3$H][3-Me-His$^2$]TRH-labelled receptors are present in discrete areas in the human brain with highest levels of binding found in the limbic structures. In human amygdala, binding of [$^3$H][3-Me-His$^2$]TRH was observed to be saturable and displayed a Kd of 7-10 nM. [$^3$H][3-Me-His$^2$]TRH bound to human pituitary with similar affinity, though fewer binding site were observed in this tissue compared to the amygdala.

Investigation of [$^3$H]TRH and [$^3$H][3-Me-His$^2$]TRH binding in rodent brain tissue has been more extensively reported. Data from such studies show that specific [$^3$H][3-Me-His$^2$]TRH binding sites are distinctly localised, and indicate that this radiolabelled peptide binds to a single population of high affinity sites on rat brain cortical membranes with a Kd of around 5 nM and that TRH competes for these sites with a $K_i$ value of around 25 nM. Similarly, [$^3$H][3-Me-His$^2$]TRH appears to bind to a single population of high-affinity sites in rat pituitary tissue with a Kd of 2.2 nM.

G-protein-coupled receptors (GPCRs) are recognized to be involved in mediating the biological actions of neuropeptides and are viewed as attractive neuropharmacological targets. To date, two GPCR subtypes for TRH have been identified in non-primates: TRH receptor 1 (TRHR1) and TRH receptor 2 (TRHR2). In addition, a third putative TRH receptor subtype was cloned in *Xenopus laevis* (xTRHR3); however, because xTRHR3 exhibited very low affinity for TRH and TRH analogs and did not discriminate among the analogs, the authors subsequently suggested that xTRHR3 is likely a receptor for another peptide.

Comparison of amino acid sequences of TRHR1 and TRHR2 from the same species shows that they have an overall homology of around 50%. In the rat, the distribution patterns of TRHR1 and TRHR2 are quite distinct. For example, TRHR1 is expressed at high levels in the pituitary and displays limited expression in the central nervous system (CNS), whereas TRHR2 is absent or present only at low levels in the pituitary and is widely distributed throughout the CNS. The distinct regional distribution of the mRNAs for TRHR1 and TRHR2, has led to the notion that TRHR1 plays a principal role in mediating the endocrine functions of TRH, while TRHR2 may be important in mediating the higher cognitive functions of TRH, as well as its effects on arousal, locomotor activity and pain perception.

Prior to cloning studies identifying two receptor subtypes for TRH in rodents it had been shown that TRH receptor protein isolated from rat brain had an isoelectric point (i.e. PI=5.5) that differed from that isolated from rat pituitary (i.e. PI=4.9), indicating that the TRH receptors in rat brain could be structurally different from those in rat pituitary.

Both TRHR1 and TRHR2 display similar high affinity for [3H][3-Me-His2]TRH and so this ligand cannot be used to discriminate between these two known TRH receptor subtypes. Similarly, TRH and many TRH analogs fail to discriminate pharmacologically between these two TRH receptor subtypes. Nevertheless, a few compounds have been reported that appear to display a degree of selectively for binding to TRHR2 versus TRHR1 in cells expressing either TRHR1 or TRHR2. Glp-Asn-Pro-DTyr-DTrp-NH2 does not displace [3H][3-Me-His2]TRH binding from cells expressing either TRHR1 or TRHR2, or rat pituitary tissue homogenate; however, it does displace [3H][3-Me-His2]TRH binding in native rat cortical tissue (Scalabrino et al., 2007).

With the discovery of TRHR2 in rodents it was initially thought that this may provide a therapeutic target for developing TRH-based neurotherapeutics for use in humans; however, TRHR2 has not been found to be present in humans. U.S. Pat. No. 6,441,133 discloses the structure of TRHR2 and claims pure protein comprising the amino acid sequence identified for TRHR2, as well as isolated recombinant TRHR2. In addition, this patent is directed to a method for assaying a test compound for its ability to bind to TRHR-2 and for assaying a test compound for its ability to alter the expression of the TRHR-2 gene. An earlier patent—U.S. Pat. No. 5,288,621—disclosed for the first time is the isolation, sequence, and expression cloning of a cDNA encoding for pituitary TRHR (i.e. TRHR1), as well as the amino acid sequence for this receptor.

Human TRHR1 is approximately 90% homologous with mouse and rat TRHR1 at the cDNA and amino acid level.

Notably, TRHR2 is not detected in humans; the only TRH receptor that has been cloned in humans is the TRHR1 subtype. Thus, to date the art indicates that in humans there is only one homogeneous TRH receptor subtype. The art also indicates that TRH receptors in human brain and pituitary are indistinguishable.

Competitive radioligand binding studies provide an important means to enable the discovery of new receptor subtypes, as well as pharmacological characterisation and classification of receptor subtypes. Receptor subtypes may be defined pharmacologically. In such cases, subtypes may be distinguished from one another on the basis of differential binding of different ligands.

The use of animal tissues and heterologous cells expressing a particular receptor subtype in drug development has its drawbacks, as there can be differences in receptor subtypes between humans and animals, such that activity in animals may not translate into efficacy in humans. Importantly, the mediation of ligand signalling through GPCRs was initially understood to involve monomeric receptors. However, this view has been revised recently with the recognition that these receptors form homo-oligomeric and hetero-oligomeric complexes that influence GPCR receptor functioning and have implications regarding drug design. For example, pairings of μ and δ subtypes of opioid receptors result in reduced affinity for ligands that are specific for each subtype. Also in relation to this, it has been suggested that data gathered from studies using isolated receptors in a non-physiological state may be misleading since the possibility of GPCR homo-hetero oligomerisation, which may be essential for ligand-receptor interactions and/or signaling, may not be possible under such circumstances. In the case of TRH receptors, constitutive and agonist-induced homo-oligomerisation has been demonstrated, as well as TRH receptor subtype hetero-oligomer formation. Thus, it is possible that formation of TRH receptor heterocomplexes may occur in native tissue, which would not be possible in the cell models expressing a single receptor subtype.

Confirmation of the binding of a potential drug to native human receptors using radioligand competition binding assays is increasingly recognised to be an important step in preclinical drug development.

It has previously been shown that Glp-Asn-Pro-D-Tyr-D-TrpNH$_2$ binds with high affinity to native TRH receptors labelled with [$^3$H][3-Me-His$^2$]TRH in rat cortical and hippocampal tissue homogenates; although it does not displace [$^3$H][3-Me-His$^2$]TRH binding from native rat pituitary tissue, CHO-TRHR1, CHO-TRHR2 or GH4 membranes (Scalabrino 2007, Hogan 2008). Glp-Asn-Pro-LTyr-LTrp-LTrp-AMC, Glp-Asn-Pro-DTyr-DTrp-DTrpAMC, Glp-Asn-Pro-LTyr-LTrp-AMC, Glp-Asn-Pro-DTyr-DTrpAMC, Glp-Asn-Pro-D-Tyr-D-TrpNH2, Glp-Asn-Pro-LTyr-LTrp-LTrpNH2, and Glp-Asn-Pro-LTyr-LTrp-NH2, display these same discriminatory properties as Glp-His-Pro-D-Tyr-D-TrpNH2. Thus, this family of peptides does not displace [$^3$H][3-Me-His$^2$]TRH binding in a GH4 pituitary cell line, which naturally expresses TRHR1; however, these peptides do displace [$^3$H][3-Me-His$^2$]TRH binding in native rat brain cortical and hippocampal and display high affinity (i.e. K$_i$ values <10$^{-6}$ M) for these binding sites in these tissues. In contrast, [3-Me-His$^2$]TRH displays high affinity for [$^3$H][3-Me-His$^2$]TRH-labelled sites in both GH4 and native rat brain cortical and hippocampal tissues (see Table 1). This family of peptides has previously been described in U.S. Pat. Nos. 7,378,397 B2 and 7,713,935 B2 as novel chemical entities that inhibit the TRH-degrading ectoenzyme (TRH-DE).

The present invention shows that Glp-Asn-Pro-D-Tyr-D-TrpNH$_2$ does not displace [$^3$H][3-Me-His$^2$]TRH binding from human pituitary tissue. Unexpectedly, however, given that research indicates the presence of only the TRHR1 subtype in humans, Glp-Asn-Pro-D-Tyr-D-TrpNH$_2$ was found to displace [$^3$H][3-Me-His$^2$]TRH binding from CNS tissue. This finding demonstrates for the first time that a TRH analog i.e. Glp-Asn-Pro-D-Tyr-D-TrpNH$_2$, binds selectively, with nM affinity, to a novel TRH receptor subtype in human CNS tissue that is pharmacologically distinct from the TRH receptor in human pituitary tissue. Notably, Glp-Asn-Pro-D-Tyr-D-TrpNH$_2$ provides a groundbreaking innovative tool to distinguish between these two, hitherto unrecognised, pharmacologically-distinct human TRH receptor subtypes.

Thus, Glp-Asn-Pro-DTyr-DTrp-NH2 and the family of structurally-related compounds defined in the claims, including Glp-Asn-Pro-LTyr-LTrp-LTrp-AMC, Glp-Asn-Pro-DTyr-DTrp-DTrpAMC, Glp-Asn-Pro-LTyr-LTrp-AMC, Glp-Asn-Pro-DTyr-DTrpAMC, Glp-Asn-Pro-D-Tyr-D-TrpNH2, Glp-Asn-Pro-LTyr-LTrp-LTrpNH2, and Glp-Asn- Pro-LTyr-LTrp-NH2, provide a unique means to recognise the existence of this novel TRH receptor subtype—no other compounds had been previously identified that can discriminate between this new central TRH receptor and the TRH pituitary receptor. Hence, there are no existing solutions to understanding how the biological effects of TRH in the CNS are mediated.

U.S. Pat. No. 5,879,896 principally claims a method of screening for a compound that inhibits binding of TRH to a human TRH receptor, or a salt thereof, comprising contacting a TRH receptor protein obtained from a cell transformed with an expression vector containing a DNA encoding a TRH receptor having the amino acid sequence of TRHR1, or a sufficient portion thereof to bind TRH, or the salt thereof, with the compound to be screened and TRH, and comparing binding between TRH and the TRH receptor in the absence and presence of the compound, wherein less binding between the TRH and the receptor in the presence of the compound than in the absence of the compound is indicative of the compound inhibiting binding between TRH and the receptor. Clearly, since Glp-Asn-Pro-DTyr-DTrp-NH2 and the structurally-related family of peptides described above were not discovered until the 2000s, the inventors of U.S. Pat. No. 5,879,896 could not have possibly anticipated the existence of a TRHR subtype that is revealed by Glp-Asn-Pro-DTyr-DTrp-NH$_2$ binding not the use of this and related compounds as described herein.

The invention described herein is relevant to the development of diagnostics and therapeutics for any TRH-related disorders, inter alia, brain and spinal injury, memory loss, spinocerebellar degeneration, pain including spinal cord pain, epilepsy, eating disorders, weight management disorders (particularly obesity), and CNS-related diseases, as well as memory loss, lethargy, anxiety disorders, jet lag, attention deficit disorders, post-traumatic syndrome and as a mood stabilizer or enhancer, and may also have application as a research tool to investigate TRH-mediated cellular processes. The present invention opens up a new area of study for pharmacological intervention of TRH signalling in the CNS and has important implications for the treatment of and development of therapeutics for CNS disorders.

The invention described herein provides for the first time a means to understand how the central therapeutic effects of TRH are mediated, as well as a method for screening for compounds that interact with this novel TRHR site that can be pharmacologically distinguished by Glp-Asn-Pro-DTyr-DTrp-NH2 and the family of structurally-related compounds defined herein.

OBJECT OF THE INVENTION

It is thus the object of the invention to provide a method of discriminating between a novel TRH receptor subtype in human brain and spinal cord, as distinct from the human pituitary TRH receptor. The invention also provides methods for screening compounds which also bind selectively to TRH receptor sites in human CNS tissue. Such compounds may find use as therapeutic compounds. In addition, the invention provides a means to investigate which biological functions of TRH are mediated through central TRH receptors and which are mediated through pituitary TRHR1 receptors.

SUMMARY OF THE INVENTION

According to the present invention there is provided use of a compound having the structure:

Glp-W-Pro-X wherein X represents residues of from 1 to 20 amino acids, which may be in the L- or D-configuration, the C-terminal amino-acid residue optionally being substituted with an amino group or aminomethyl coumarin (AMC),
and W represents a natural or un-natural or amino-acid,
in a method of discriminating between a TRH receptor subtype in human CNS tissue and a TRH receptor subtype in human pituitary tissue.

X may represent residues of from 1 to 15, or 1 to 10, or 1 to 7, or 1 to 5 or 1 to 3 amino acids.

The invention also provides use of a compound as defined above in the diagnosis and treatment of human CNS disorders including but not limited to amyotropic lateral sclerosis brain and spinal injury, stroke, memory loss, spinocerebellar degeneration, pain, neurodegeneration, chronic fatigue syndromes, narcolepsy, lethargy, sedation secondary to drugs, chemo- or radiation therapy, sedative intoxication/respiratory distress, recovery from general anaesthesia, attention deficit disorder, epilepsy, obesity, diabetes, psychiatric disorders, disorders of mood, depression, bipolar affective disorder, disturbances of circadian rhythm (e.g. jet lag), anxiety disorders, Alzheimer's disease and other dementias with cognition deficits, frontotemporal dementia, seizure disorders, obesity, motor neuron disorders, and Parkinson's disorder.

In a further aspect the invention provides a method of screening for therapeutic agents capable of binding to a TRH receptor subtype in human CNS tissue, the receptor subtype being distinguishable from the pituitary TRH receptor subtype on the basis of selective binding to a compound as defined above, comprising determining the ability of the test therapeutic agent to bind to the TRH receptor in human CNS tissue.

The invention also relates to an isolated TRH receptor subtype from human CNS tissue, the receptor displaying selective binding to a compound as defined above.

The invention also provides a cell expressing an isolated TRH receptor subtype from human CNS tissue, the receptor displaying selective binding to a compound as defined above. The cell may be an *E. coli, B. subtilis*, yeast, insect or animal cell.

The isolated receptor as defined above, or the cell as defined above may be used for research and development of diagnostic and therapeutic applications in disease. In particular they may be used to identify novel diagnostic and therapeutic compounds, assays, methods or uses in relation to CNS diseases.

In the compounds used in the invention the X amino acids may be in the L- or D-configuration.

X may represent amino acid residues having neutral side chains

W may represent the side chain of an amino acid residue in which the R group is neutral, or charged.

W may be asparagine in the D-configuration.

W may be asparagine in the L-configuration.

The compound may be selected from:
Glp-Asn-Pro-D-TyrNH$_2$,
Glp-Asn-Pro-D-TrpNH$_2$,
Glp-Asn-Pro-D-Trp-D-Ser-D-TyrNH$_2$,
Glp-Asn-Pro-D-Trp-D-TyrNH$_2$,
Glp-Asn-Pro-D-Tyr-D-TrpNH$_2$, Glp-Asn-Pro-D-Tyr-D-Trp-D-TrpNH$_2$
Glp-Asn-Pro-D-Tyr-D-TrpAMC,
Glp-Asn-Pro-D-Trp-D-TyrAMC,
Glp-Asn-Pro-D-Tyr-D-Trp-D-TrpAMC,
Glp-Asn-Pro-D-Phe-D-TyrAMC,
Glp-Asn-Pro-D-Ala-D-TrpAMC,
Glp-Asn-Pro-D-Val-D-Tyr-D-TrpAMC,
Glp-Asn-Pro-D-TrpAMC,
Glp-His-Pro-D-Tyr-D-TrpNH$_2$.
Glp-Asn-Pro-LTyr-LTrp-LTrp-AMC
Glp-Asn-Pro-LTyr-LTrp-AMC
Glp-Asn-Pro-LTyr-LTrp-NH2.

Particularly preferred is Glp-Asn-Pro-D-Tyr-D-TrpNH$_2$.

BRIEF DESCRIPTION OF THE INVENTION

Confirmation that a compound binds to its targeted receptor in native human tissue is a critical step in progressing compounds to clinical development. This is especially important since the apparent pharmacology of recombinant receptors may not reflect that of the native human target. A limited number of radioligand binding studies employing human brain tissue have previously been described that show [$^3$H][3-Me-His$^2$]TRH labels receptors in human pituitary and in discrete areas of the human brain.

To date, two G Protein-Coupled Receptor (GPCR) subtypes have been identified for TRH in some non-human species: TRH receptor 1 (TRHR1) and TRH receptor 2 (TRHR2). Both receptors bind TRH and 3-Me-His$^2$TRH with similar high affinity. Thus, these ligands cannot be used to discriminate pharmacologically between these two known TRH receptor subtypes.

The different regional distributions of TRHR1 and TRHR2 mRNA in rat led to the notion that TRHR1 plays a principal role in mediating the endocrine functions of TRH, while TRHR2 may be important in mediating its CNS actions, which are independent of the hypothalamic-pituitary-thyroid axis. It was initially thought that TRHR2 may provide a therapeutic target for developing TRH-based neurotherapeutics for use in humans, but it was subsequently found to be absent from humans. The blastp algorithm [http://blast.ncbi.nlm.nih.gov/], confirms that no ortholog exists in human for mouse or rat TRHR2 and that the closest is TRHR1 with 58% and 55% identity to mouse and rat TRHR2, respectively. Thus, research to date indicates that in humans there is only one TRH receptor i.e. TRHR1.

Glp-Asn-Pro-D-Tyr-D-TrpNH$_2$ has previously been shown to displace [$^3$H][3-Me-His$^2$]TRH binding to native rat cortical and hippocampal tissue but not pituitary tissue (Scalabrino 2007; Hogan 2008), consistent with its ability to evoke central pharmacological actions of TRH in rat without stimulating endocrine effects in vivo. This suggested that Glp-Asn-Pro-D-Tyr-D-TrpNH$_2$ may be binding to TRHR2; however, it did not displace [$^3$H][3-Me-His$^2$]TRH binding in heterologous cells expressing TRHR2 (Hogan 2008). Differences in the binding properties of native and heterologously expressed TRHR2 receptors could potentially be explained, however, by differences in post-translational modification or receptor activity-modifying proteins (RAMPs).

The present invention discloses that Glp-Asn-Pro-D-Tyr-D-TrpNH2 binds to TRH receptors in human brain and spinal cord, but not human pituitary tissue.

In the case of the human tissue Glp-Asn-Pro-D-Tyr-D-TrpNH$_2$ is clearly not binding to TRHR2 since this TRH receptor subtype is not present in humans. Thus, this pentapeptide is binding to a hitherto unidentified TRH receptor subtype in human CNS that is distinct from the TRH receptor present in human pituitary tissue.

The discovery of a novel TRH receptor in human CNS that can be pharmacologically distinguished from that in the pituitary represents a major finding in the TRH pharmacology field. This opens up new opportunities for exploring the neuropharmacological actions of TRH and identifies a potentially important therapeutic target with respect to drug development in the CNS arena.

The invention provides a method of discriminating between a TRH receptor subtype in human CNS tissue and a TRH receptor subtype in human pituitary tissue. According to one aspect, the present invention will provide a method of screening for therapeutic agents for the treatment of CNS-related disorders, which are capable of binding to a TRH receptor subtype in human CNS tissue, the receptor subtype being distinguishable from the pituitary TRH receptor subtype. The invention will also provide an isolated TRH receptor subtype displaying selective binding for Glp-Asn-Pro-D-Tyr-D-TrpNH$_2$, which can be used as a target for diagnostic and therapeutic applications in human disease, as well as a cell expressing this TRH receptor subtype, which can be used in research and development of diagnostic and therapeutic applications in human disease. The invention also provides a means to purify and characterise the novel TRH receptor subtype. In a further aspect of the invention compounds of the invention may be used in the treatment of CNS-related disorders. Compounds of the invention may be administered by oral, parenteral, intramuscular (i.m.), intraperitoneal (i.p.), intravenous (i.v.) or subcutaneous (s.c.) injection, nasal, vaginal, rectal or sublingual routes of administration and formulated in dosage forms appropriate for each route of administration. Such compounds may be administered in combination with one or more other pharmacologically active substances.

EXAMPLES

Pharmacologically distinct receptor subtypes may be evidenced by discriminatory ligand binding. Herein, radioligand binding studies are described that show Glp-Asn-Pro-D-Tyr-D-TrpNH$_2$ binds to TRH receptors in human brain and spinal cord, but not pituitary, demonstrating the presence of pharmacologically distinct TRH receptor subtypes in human CNS and pituitary.

General Procedures for Radioligand Binding Studies

To investigate the binding of Glp-Asn-Pro-D-Tyr-D-TrpNH$_2$ in human tissue, radioligand binding studies were carried out employing [$^3$H][3-Me-His$^2$]TRH to label TRH receptors in cortical, hippocampal, spinal cord and pituitary tissue membranes from human tissue.

All chemicals were purchased from Sigma-Aldrich unless otherwise stated. Glp-Asn-Pro-D-Tyr-D-TrpNH$_2$ and all other peptides except TRH and [3-Me-His2]TRH were custom synthesized under CDA by the American Peptide Company, Sunnyvale, Calif., U.S.A. [$^3$H][3-Me-His$^2$]TRH was obtained from Perkin Elmer, Boston, Mass., U.S.A.

Competition binding assays using human tissue prepared from individual donors with no history of neurological disease were carried out essentially as previously described (Kelly et al., 2002; Scalabrino et al., 2007; Hogan et al., 2008) by incubating membrane suspension, [$^3$H][3-Me-His$^2$]TRH, and increasing concentrations of peptide for 5 h at 4° C. Non-specific binding (NSB) was determined in the presence of 10 µM TRH. Separation of bound and free ligand was achieved by vacuum filtration through GF/C or GF/B filters, followed by washing with 3×5 ml of ice-cold NaCl or Tris-HCl buffer. The radioactivity retained on the filters was measured by liquid scintillation counting.

In competition binding experiments TRH displaced [$^3$H][3-Me-His$^2$]TRH from both CNS tissue and pituitary tissue with an IC$_{50}$ value in the order of $10^{-8}$ M. Notably, unlike TRH, Glp-Asn-Pro-D-Tyr-D-TrpNH$_2$ did not displace [$^3$H][3-Me-His$^2$]TRH binding from pituitary membranes, but it did displace this label from hippocampal membranes with an IC$_{50}$ value in the order of $10^{-8}$ M. The same pharmacological profile is displayed by Glp-Asn-Pro-D-Tyr-D-TrpNH$_2$ in competition experiments carried out under the same conditions; in this case IC$_{50}$ is in the order of $10^{-7}$ M for CNS tissue. These results reveal for the first time that [$^3$H][3-Me-His$^2$]TRH labels a population of TRH receptors in human CNS tissue that are pharmacologically distinct from those in human pituitary and that Glp-Asn-Pro-D-Tyr-D-TrpNH$_2$ is a potent discriminating ligand for these non-pituitary sites.

Affinity chromatography can be used to purify the novel TRH receptor subtype. This technology is well recognized as a means of protein purification and has been successfully employed in the purification of other receptors. Briefly, in this technique, Glp-Asn-Pro-D-Tyr-D-TrpNH$_2$, or one of its analogs, could be employed as an affinity ligand. In this case, Glp-Asn-Pro-D-Tyr-D-TrpOH, for example, can be attached to a suitable solid phase support, such as an agarose derivative containing free amino groups. The purification procedure firstly involves solubilization of the receptor from a membrane preparation, which can be achieved using a suitable detergent such as CHAPS or octyl glucoside. Subsequently, this solubilised preparation is passed down a Glp-Asn-Pro-D-Tyr-D-TrpNH$_2$-derivatized column, which retains the protein of interest. Other proteins would be washed from the column using a suitable buffer, such as phosphate or Tris buffer. The receptor protein can then be

TABLE 1

Displacement of [$^3$H][3-Me-His$^2$]TRH by a set of related peptides in native rat tissues and cell models. Cortical and hippocampal results are K$_i$ values; cell model results are IC$_{50}$ values.

| Peptide | Cortical membranes N = 3-6 | Hippocampal membranes N = 3-6 | GH4 cell membranes N = 2 | Membranes from Chinese Hamster Ovary cells transfected with TRHR1 N = 2 |
|---|---|---|---|---|
| Glp-Asn-Pro-LTyr-LTrp-LTrp-AMC | $2 \times 10^{-6}$ | $8.8 \times 10^{-9}$ | $>10^{-4}$ | N.D. |
| Glp-Asn-Pro-DTyr-DTrp-DTrp-AMC | $2.5 \times 10^{-8}$ | $3 \times 10^{-8}$ | $>10^{-4}$ | N.D. |
| Glp-Asn-Pro-LTyr-LTrp-AMC | $3.3 \times 10^{-7}$ | $8 \times 10^{-8}$ | $>10^{-4}$ | N.D. |
| Glp-Asn-Pro-DTyr-DTrp-AMC | $1.7 \times 10^{-9}$ | $2.2 \times 10^{-8}$ | $>10^{-4}$ | N.D. |
| Glp-Asn-Pro-LTyr-LTrp-NH2 | $1.1 \times 10^{-7}$ | $1.2 \times 10^{-7}$ | $>10^{-4}$ | $>10^{-4}$ |
| Glp-Asn-Pro-D-Tyr-D-TrpNH2 | $6.8 \times 10^{-9}$ | $1.1 \times 10^{-8}$ | $>10^{-4}$ | $>10^{-4}$ |
| [3-Me-His2]TRH | $7.4 \times 10^{-8}$ | $3.4 \times 10^{-8}$ | $1.12 \times 10^{-8}$ | $1.75 \times 10^{-8}$ |

N.D. = not determined.

Radioligand competition binding assays may be undertaken to screen for potential ligands and new therapeutic agents binding to the novel TRH receptor subtype. For example, membrane suspensions prepared as previously described (Kelly et al., 2002; Scalabrino et al., 2007; Hogan et al., 2008) may be incubated with radiolabelled Glp-Asn-Pro-D-Tyr-D-TrpNH$_2$ or one of its analogs and increasing concentrations of test compound for 5 h at 4° C. Non-specific binding (NSB) can be determined in the presence of 10 μM TRH. Bound and free ligand may be separated by vacuum filtration through GF/C filters, followed by washing with 3×5 ml of ice-cold aqueous NaCl or Tris-HCl buffer. The radioactivity retained on the filters is measured by liquid scintillation counting. Subtraction of NSB from Total binding (TB) provides a measure of specific binding (SB) from which the affinity for the novel TRH receptor subtype can be calculated.

The art indicates that further analysis of the biological responses after ligand binding can be undertaken to provide additional information regarding the characteristics of the ligand or new therapeutic agent. For example, G-protein-dependent functional assays can be undertaken to determine downstream signalling pathways and enable discrimination between full or partial agonists, neutral antagonists, inverse agonists and allosteric regulators. In such assays the accumulation of non-hydrolysable GTP analog, such as [$^{35}$S]-GTPγS, on the plasma membrane prepared from cells expressing the GPCR of interest is typically measured after agonist stimulation. Cell-based functional assays designed to measure a particular second messenger, such as cAMP or inositol phosphate, may also be employed in characterising cellular responses to ligand binding.

eluted by washing the column with a suitable eluant, such as a solution of Glp-Asn-Pro-D-Tyr-D-TrpNH$_2$ or TRH or 3-Me-His$^2$TRH. The eluting ligand can be removed for example by dialysis and the protein of interest may be concentrated by a technique such as lyophilisation. SDS-PAGE can then be undertaken to carry out preliminary characterization. Full or partial sequence of the purified protein would then be obtained.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

REFERENCES

Scalabrino G A, Hogan N, O'Boyle K M, Slator G R, Gregg D J, Fitchett C M, Draper S M, Bennett G W, Hinkle P M, Bauer K, Williams C H, Tipton K F, Kelly J A. Discovery of a dual action first-in-class peptide that mimics and enhances CNS-mediated actions of thyrotropin-releasing hormone, Neuropharmacology. 2007 June; 52(7):1472-81.

Hogan N, O'Boyle K M, Hinkle P M, Kelly J A. A novel TRH analog, Glp-Asn-Pro-D-Tyr-D-TrpNH$_2$, binds to [$^3$H][3-Me-His$^2$]TRH-labelled sites in rat hippocampus and cortex but not pituitary or heterologous cells expressing TRHR1 or TRHR2. Neurosci Lett. 2008 Jan. 24; 431(1): 26-30.

Kelly J A, Slator G R, O'Boyle K M. Pharmacological distinct binding sites in rat brain for [3H]-thyrotropin-releasing hormone (TRH) and [$^3$H][3-methyl-histidine$^2$] TRH. Biochem. Pharmacol. 2002 Jun. 15; 63 (12): 2197-2206.

The invention claimed is:

1. A method of detecting a human central nervous system (CNS) TRH receptor subtype in a human tissue, the method comprising incubating a human tissue sample suspected of comprising the TRH receptor subtype with a compound having the structure:

Glp-W-Pro-X, wherein X represents residues of from 1 to 20 amino acids, which may be in the L- or D-configuration, the C-terminal amino-acid residue optionally being substituted with an amino group or aminomethyl coumarin (AMC), and W represents a natural or an un-natural amino-acid, and detecting any compound bound to the human tissue sample.

2. A method to purify a human central nervous system (CNS) TRH receptor subtype from a human tissue sample, the method comprising contacting a compound having the structure:—

Glp-W-Pro-X, wherein X represents residue of from 1 to 20 amino acids, which may be in the L- or D-configuration, the C-terminal amino-acid residue optionally being substituted with an amino group or aminomethyl coumarin, and W represents a natural or an un-natural amino-acid, with the human sample and purifying from the human sample the TRH receptor bound to the compound.

3. The method of claim 1 or 2, wherein the human tissue sample is isolated from a human with a CNS disorder selected from the group of brain and spinal injury, stroke, memory loss, spinocerebellar degeneration, pain, chronic fatigue syndromes, narcolepsy, lethargy, sedation secondary to drugs, chemo- or radiation therapy, sedative intoxication/respiratory distress, recovery from general anaesthesia, neurodegeneration, epilepsy, obesity, diabetes, attention deficit disorder, psychiatric disorders, disorders of mood, depression, bipolar affective disorder, disturbances of circadian rhythm (e.g. jet lag), anxiety disorders, Alzheimer's disease and other dementias with cognition deficits, frontotemporal dementia, seizure disorders, obesity, motor neuron disorders, Parkinson's and CNS related diseases.

4. The method of claim 1, or 2 wherein the compound is selected from a compound having the structure:—

Glp-Asn-Pro-D-TyrNH$_2$,
Glp-Asn-Pro-D-TrpNH$_2$,
Glp-Asn-Pro-D-Trp-D-Ser-D-TyrNH$_2$,
Glp-Asn-Pro-D-Trp-D-TyrNH$_2$,
Glp-Asn-Pro-D-Tyr-D-TrpNH$_2$,
Glp-Asn-Pro-D-Tyr-D-Trp-D-TrpNH$_2$
Glp-Asn-Pro-D-Tyr-D-TrpAMC,
Glp-Asn-Pro-D-Trp-D-TyrAMC,
Glp-Asn-Pro-D-Tyr-D-Trp-D-TrpAMC,
Glp-Asn-Pro-D-Phe-D-TyrAMC,
Glp-Asn-Pro-D-Ala-D-TrpAMC,
Glp-Asn-Pro-D-Val-D-Tyr-D-TrpAMC,
Glp-Asn-Pro-D-TrpAMC,
Glp-His-Pro-D-Tyr-D-TrpNH$_2$,
Glp-Asn-Pro-LTyr-LTrp-LTrp-AMC,
Glp-Asn-Pro-LTyr-LTrp-AMC, or
Glp-Asn-Pro-LTyr-LTrp-NH$_2$.

5. The method as claimed in claim 4 wherein the compound is selected from a compound of the structure:—

Glp-Asn-Pro-D-Tyr-D-TrpNH$_2$,
Glp-Asn-Pro-D-Tyr-D-Trp-D-TrpNH$_2$,
Glp-Asn-Pro-D-Tyr-D-TrpAMC,
Glp-His-Pro-D-Tyr-D-TrpNH$_2$,
Glp-Asn-Pro-LTyr-LTrp-LTrp-AMC,
Glp-Asn-Pro-LTyr-LTrp-AMC, or
Glp-Asn-Pro-LTyr-LTrp-NH$_2$.

6. The method as claimed in claim 4 wherein the compound is of the structure Glp-Asn-Pro-D-Tyr-D-TrpNH$_2$.

7. The method as claimed in claim 4 wherein the compound is selected from a compound of the structure:—

Glp-Asn-Pro-D-Tyr-D-TrpNH$_2$,
Glp-Asn-Pro-D-Tyr-D-Trp-D-TrpNH$_2$,
Glp-Asn-Pro-D-Tyr-D-TrpAMC, or
Glp-His-Pro-D-Tyr-D-TrpNH$_2$.

* * * * *